(12) United States Patent
Kreindel et al.

(10) Patent No.: US 6,662,054 B2
(45) Date of Patent: Dec. 9, 2003

(54) METHOD AND SYSTEM FOR TREATING SKIN

(75) Inventors: Michael Kreindel, Haifa (IL); Amir Waldman, Yarqona (IL)

(73) Assignee: Syneron Medical Ltd., Or Akiva (IL)

( * ) Notice: Subject to any disclaimer, the term of this patent is extended or adjusted under 35 U.S.C. 154(b) by 0 days.

(21) Appl. No.: 10/105,885

(22) Filed: Mar. 26, 2002

(65) Prior Publication Data

US 2003/0187488 A1 Oct. 2, 2003

(51) Int. Cl.[7] .................................................. A61F 2/00
(52) U.S. Cl. ........................ 607/101; 607/108; 607/154
(58) Field of Search .............................. 607/96, 98, 99, 607/101, 102, 104, 108–112, 154–156; 606/41, 42

(56) References Cited

U.S. PATENT DOCUMENTS

| | | | | |
|---|---|---|---|---|
| 4,140,130 A | * | 2/1979 | Storm, III | 607/154 |
| 5,948,009 A | * | 9/1999 | Tu | 607/96 |
| 5,961,475 A | | 10/1999 | Guitay | |
| 6,047,215 A | * | 4/2000 | McClure et al. | 607/101 |
| 6,068,583 A | * | 5/2000 | Sigl | 493/60 |
| 6,273,884 B1 | | 8/2001 | Altshuler et al. | |
| 6,336,926 B1 | * | 1/2002 | Goble | 606/3 |
| 6,350,276 B1 | * | 2/2002 | Knowlton | 607/104 |
| 6,470,216 B1 | * | 10/2002 | Knowlton | 607/101 |
| 6,500,141 B1 | * | 12/2002 | Irion et al. | 604/22 |

FOREIGN PATENT DOCUMENTS

| | | |
|---|---|---|
| WO | WO 98 05286 | 2/1998 |
| WO | WO 00 48644 | 8/2000 |
| WO | WO 01 58373 | 8/2001 |
| WO | WO 01 80756 | 11/2001 |

* cited by examiner

*Primary Examiner*—Roy D. Gibson
(74) *Attorney, Agent, or Firm*—Browdy and Neimark, P.L.L.C.

(57) ABSTRACT

A method and system for treating skin. The method comprises deforming the skin so that a region of skin protrudes from surrounding skin, and applying radio frequency (RF) energy to the skin. The system comprises a skin deformer that deforms a region of skin so that a region of skin protrudes out from surrounding skin. The system also comprises one or more RF elemodes configured to apply RF energy to the skin. The invention may be used to treat subcutaneous adipose tissue and cartage.

18 Claims, 3 Drawing Sheets

METHOD AND SYSTEM FOR TREATING SKIN

FIELD OF THE INVENTION

The invention relates to methods and devices for treating skin.

BACKGROUND OF THE INVENTION

Skin tissue consists of an outer epidermal layer overlying a dermal layer that is in contact with a layer of subcutaneous adipose tissue. Massaging of the skin has long been known to improve the blood circulation in the subcutaneous adipose tissue. Various types of massaging devices have been used for treating adipose tissue. U.S. Pat. No. 5,961,475 discloses a massaging device in which negative pressure is applied to the skin together with massaging. The combined treatment increases the blood circulation in the subcutaneous adipose tissue and breaks connections between adipose cells in the tissue.

U.S. Pat. No. 6,273,884 to Altshuler et al. discloses simultaneous application of optical energy and negative pressure to the skin in order to treat a skin defect.

SUMMARY OF THE INVENTION

The present invention is based upon the finding that skin heating improves skin elasticity and oxygen dissociation from hemoglobin in the blood. Improved skin elasticity allows more aggressive massaging of the skin and oxygen dissociation from hemoglobin causes fat destruction. In order to obtain these beneficial effects of heating on subcutaneous adipose tissue, it is necessary to conduct heat applied to the skin surface into the skin tissue to a depth of about 1 cm without damaging the skin.

The present invention is also based upon the findings that deforming a region of skin so that the region protrudes out from surrounding skin enhances heat delivery to the subcutaneous adipose tissue and cartilage.

In accordance with the invention, a region of skin to be treated is deformed so that the region protrudes out from surrounding skin, and radio-frequency (RF) energy is applied to the protrusion by applying one or more RF electrodes to the skin surface. In a preferred embodiment, the region of skin is deformed by applying a negative pressure to the region of the skin. Applying negative pressure to skin also increases the blood circulation in the skin. The skin surface can be hydrated to improve electrode coupling.

The RF electrodes may optionally be used to monitor skin impedance during the treatment. Since increasing skin temperature leads to a change in impedance, monitoring the skin impedance allows the temperature distribution in the skin to be followed so that the parameters of the treatment (intensity of the pressure or the RF energy) may be altered to optimize the treatment.

Thus, in a first aspect of the invention there is provided a method for carrying out a treatment of skin, comprising, for each of one or more regions of the skin:

(a) deforming the skin so that the region of skin protrudes from surrounding skin;

(b) applying radio frequency (RF) energy to the skin.

In a further aspect of the invention there is provided a system for treating skin, comprising:

(a) a skin deformer deforming the skin so that a region of skin protrudes out from surrounding skin; and (b) one or more RF electrodes configured to apply RF energy to the skin.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 1:
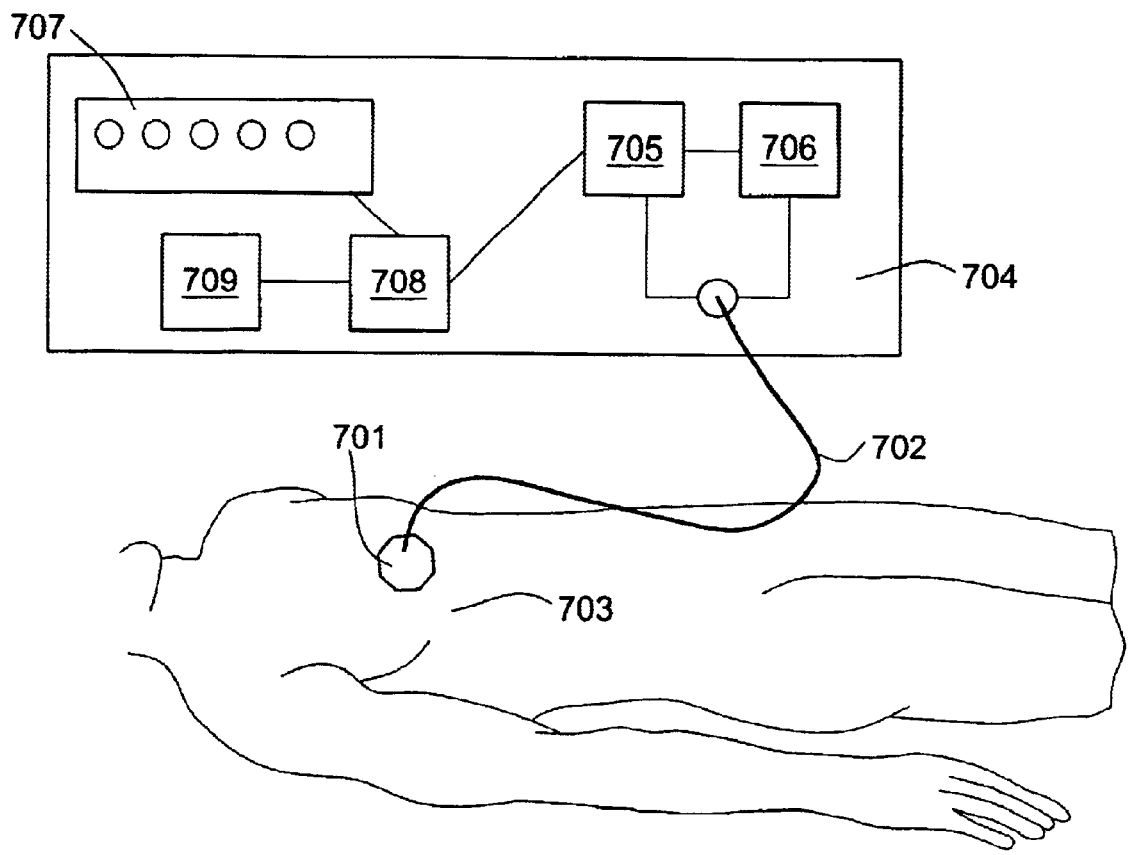
FIG. 1 shows a system for treatment of skin in accordance with the invention.
Figure 2:
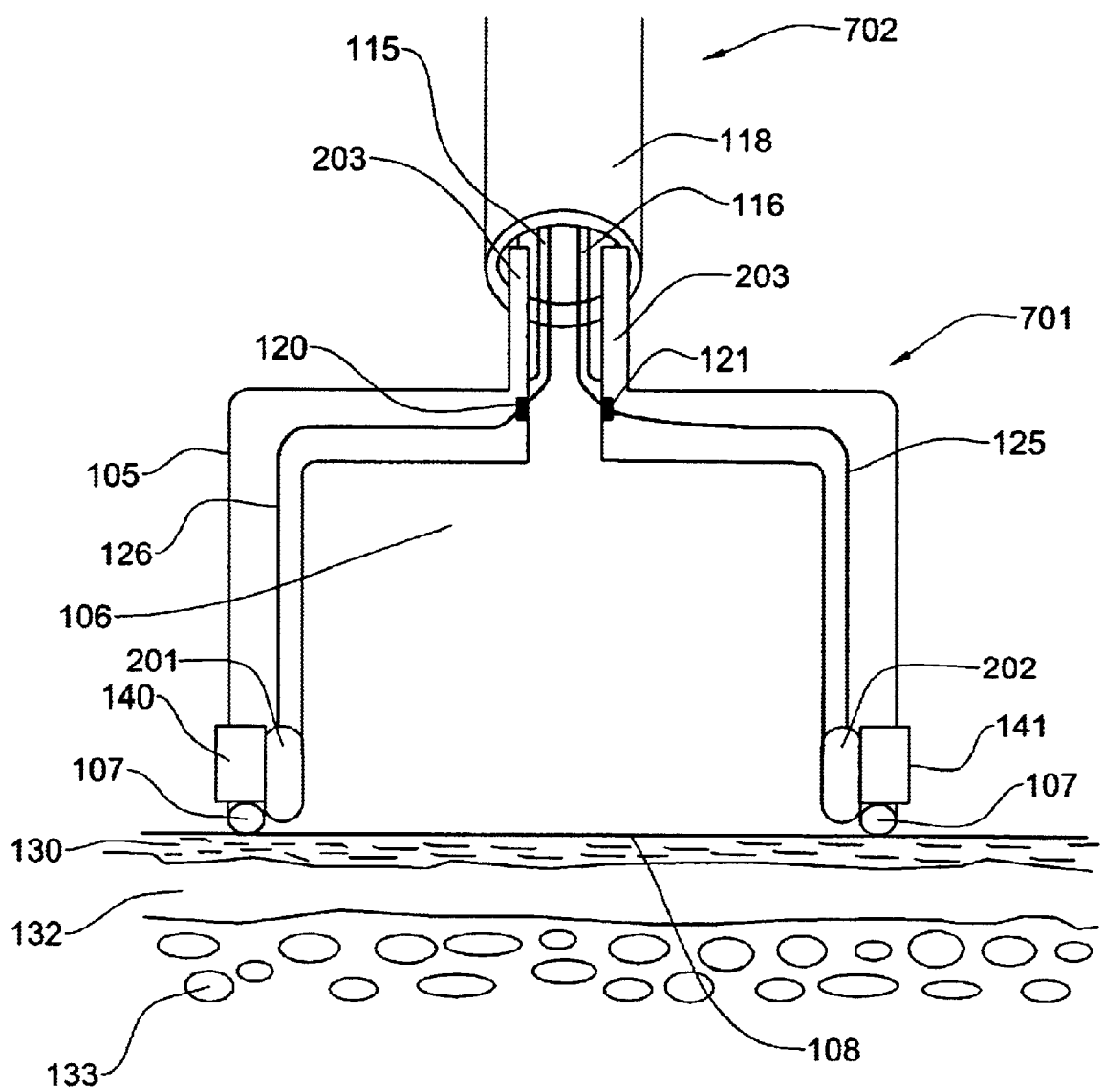
FIG. 2 shows an applicator for applying negative pressure and RF energy to skin in accordance with the invention.

Referring to FIGS. 1 and 2, a device for applying negative pressure and RP energy to skin in accordance with the invention is shown. An applicator 701, to be described in detail below, is configured to be applied to a region the skin of an individual 703 in a region to be treated. The applicator 701 is connected to a control unit 704 via a cable 702. A pump 706 is used to evacuate air from an interior chamber 106 in the applicator via a tube 118 extending from the pump 706 along the cable 702 to the interior chamber 106. The control unit 703 includes a power source 705. The power source 705 is connected to a pair of RF electrodes 201 and 202 in the applicator 701 via wires 115 and 116 that pass through the tube 118 in the cable 702. For example, the processor 708 may monitor the RF current and voltage by an impedance meter 709 that measures the impedance across the electrodes 201 and 202, and calculate the skin temperature during treatment. The control unit 701 has an input device such as a keypad 707 that allows an operator to input selected values of parameters of the treatment, such as the power of the RF energy or the intensity of the negative pressure. The control unit 701 optionally contains a processor 708 for monitoring and controlling various functions of the device. For example, the processor 708 may monitor the RF current voltage and calculate the skin temperature during the treatment.

Referring still to FIG. 2, the tube 118 is dimensions to fit snugly on a nipple 203 located on the top of the housing 105. The wires 115 and 116 are attached to terminal 120 and 121, respectively. The terminals 120 and 121 are in electrical contact with the electrodes 201 and 202, respectively, via wires 125 and 126, respectively, in the housing 105. Thermoelectric coolers 140 and 141 cool the electrodes 201 and 202 in order to prevent burning of the skin.

Figure 3:
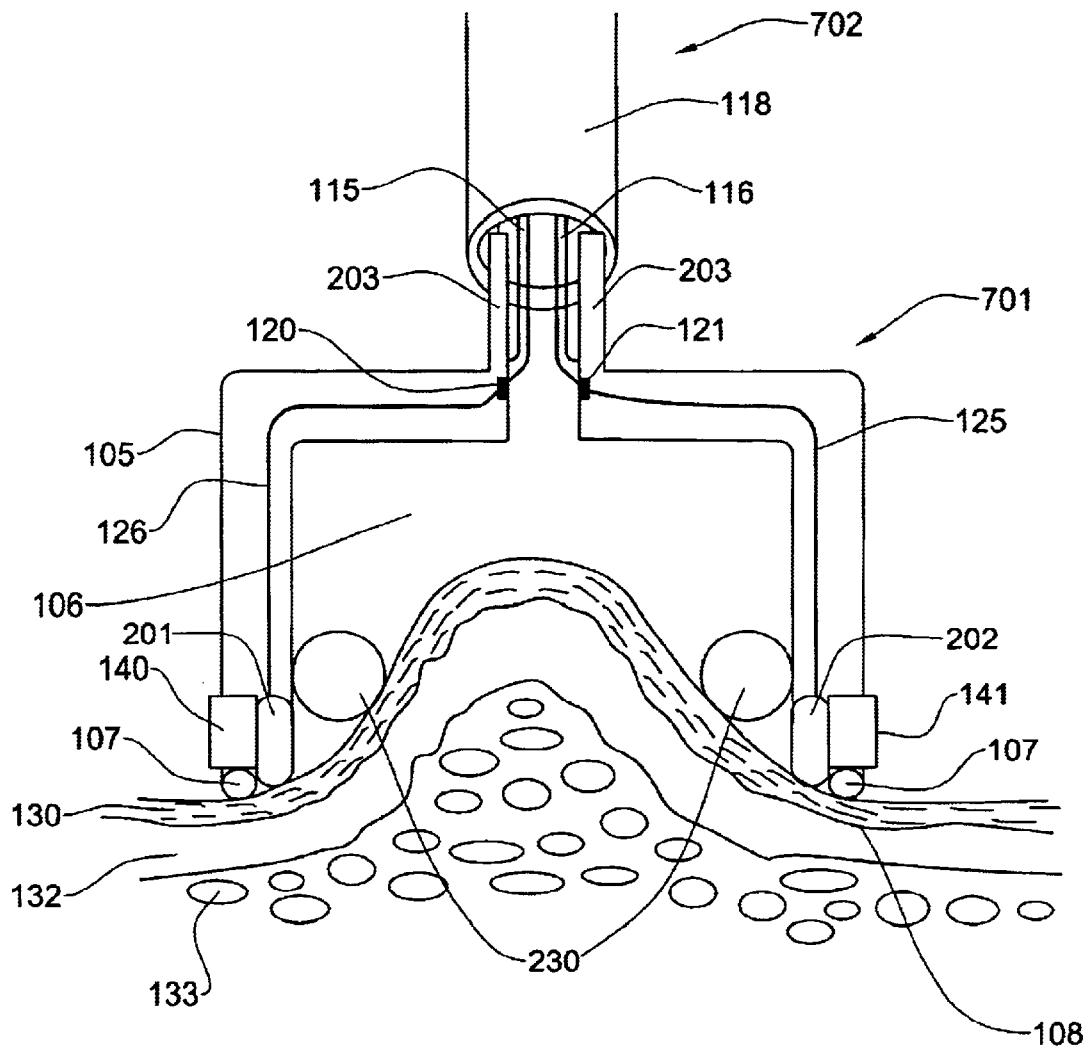
FIG. 3 shows deformation of skin with the applicator of FIG. 2.

Activating the pump 706 partially evacuates the interior 106 of the applicator, so as to create a negative pressure in the interior of the applicator 701. FIG. 3 shows the applicator and the region of skin after partial evacuation of the interior 106 of the applicator. The region 108 of the skin in contact with the interior of the applicator has been deformed so as to protrude into the interior of the applicator. In this configuration of the skin, the subcutaneous adipose tissue 133 is brought closer to the RF electrodes 201 and 202. RF energy is then applied to the skin by the electrodes. A skin massager 230 may also be associated with the applicator for massaging the skin during the RF treatment.

Using the system of the invention to treat a region of skin having an area of about 10 cm$^2$, the following exemplary parameter values may be used:

RF frequency: 0.3–10MHz.

Average output power: from about 1 to about 300 W.

Pressure in the interior chamber 106: from 0.2 to 1 atmosphere.

What is claimed is:

1. A method for carrying out a treatment of skin, comprising, for each of one or more regions of the skin:
   (a) deforming the skin so that the region of skin protrudes from surrounding skin;
   (b) applying radio frequency (RF) energy to the skin; and
   (c) massaging the skin.

2. The method according to claim 1 further comprising cooling the skin.

3. The method according to claim 1 wherein deforming the skin comprises applying a negative pressure to the skin.

4. The method according to claim 1 wherein the treatment involves treating subcutaneous adipose tissue or cartilage.

5. The method according to claim 1 wherein the frequency of the RF energy is from 0.3 to 10 MHz.

6. The method according to claim 1 wherein the power of the RF energy is from 1 to 300 W.

7. The method according to claim 3 wherein the negative pressure is from 0.2 to 1 atmosphere.

8. A system for treating skin, comprising:
   (a) a skin deformer deforming the skin so that a region of skin protrudes out from surrounding skin;
   (b) one or more RF electrodes configured to apply RF energy to the skins;
   (c) a massage for massaging the skin.

9. The system according to claim 8 wherein the skin is deformed by applying a negative pressure to the skin.

10. The system according to claim 9 wherein the skin deformer comprises:
    (a) an applicator configured to be applied to the skin having a housing incompletely enclosing a space such that when applied to the skin the space is completely enclosed;
    (b) a pump removing air from the space when the applicator is applied to the skin.

11. The system according to claim 8 further comprising a cooler for cooling the skin.

12. The system according to claim 8 further comprising an impedance meter for measuring an impedance across one or more RF electrode pairs.

13. The system according to claim 8 further comprising a processor configured to determine a heat distribution in the skin based upon one or more impedance measurements.

14. The system according to claim 13 wherein the processor is further configured to determine one or more parameters of the RF energy based upon one or more impedance measurements.

15. The system according to claim 14 wherein the one or more parameters are selected from the group comprising a pulse duration of the RF energy, a frequency of the RF energy, a power of the RF energy, and a delay time between cooling the skin an and-application of the RF energy.

16. The system according to claim 8 wherein the frequency of the RF energy is from 0.3 to 10 MHz.

17. The system according to claim 8 wherein the power of the RF energy is from 1 to 300 W.

18. The system according to claim 9 wherein the negative pressure is from 0.2 to 1 atmosphere.

* * * * *

(12) EX PARTE REEXAMINATION CERTIFICATE (9814th)
United States Patent
Kreindel et al.

(10) Number: US 6,662,054 C1
(45) Certificate Issued: Aug. 27, 2013

(54) METHOD AND SYSTEM FOR TREATING SKIN

(75) Inventors: Michael Kreindel, Haifa (IL); Amir Waldman, Yarqona (IL)

(73) Assignee: Syneron Medical Ltd., Or Akiva (IL)

Reexamination Request:
No. 90/012,629, Sep. 14, 2012

Reexamination Certificate for:
Patent No.: 6,662,054
Issued: Dec. 9, 2003
Appl. No.: 10/105,885
Filed: Mar. 26, 2002

(51) Int. Cl.
*A61F 2/00* (2006.01)

(52) U.S. Cl.
USPC .............................. 607/101; 607/108; 607/154

(58) Field of Classification Search
None
See application file for complete search history.

(56) References Cited

To view the complete listing of prior art documents cited during the proceeding for Reexamination Control Number 90/012,629, please refer to the USPTO's public Patent Application Information Retrieval (PAIR) system under the Display References tab.

*Primary Examiner* — Glenn K. Dawson

(57) ABSTRACT

A method and system for treating skin. The method comprises deforming the skin so that a region of skin protrudes from surrounding skin, and applying radio frequency (RF) energy to the skin. The system comprises a skin deformer that deforms a region of skin so that a region of skin protrudes out from surrounding skin. The system also comprises one or more RF elemodes configured to apply RF energy to the skin. The invention may be used to treat subcutaneous adipose tissue and cartage.

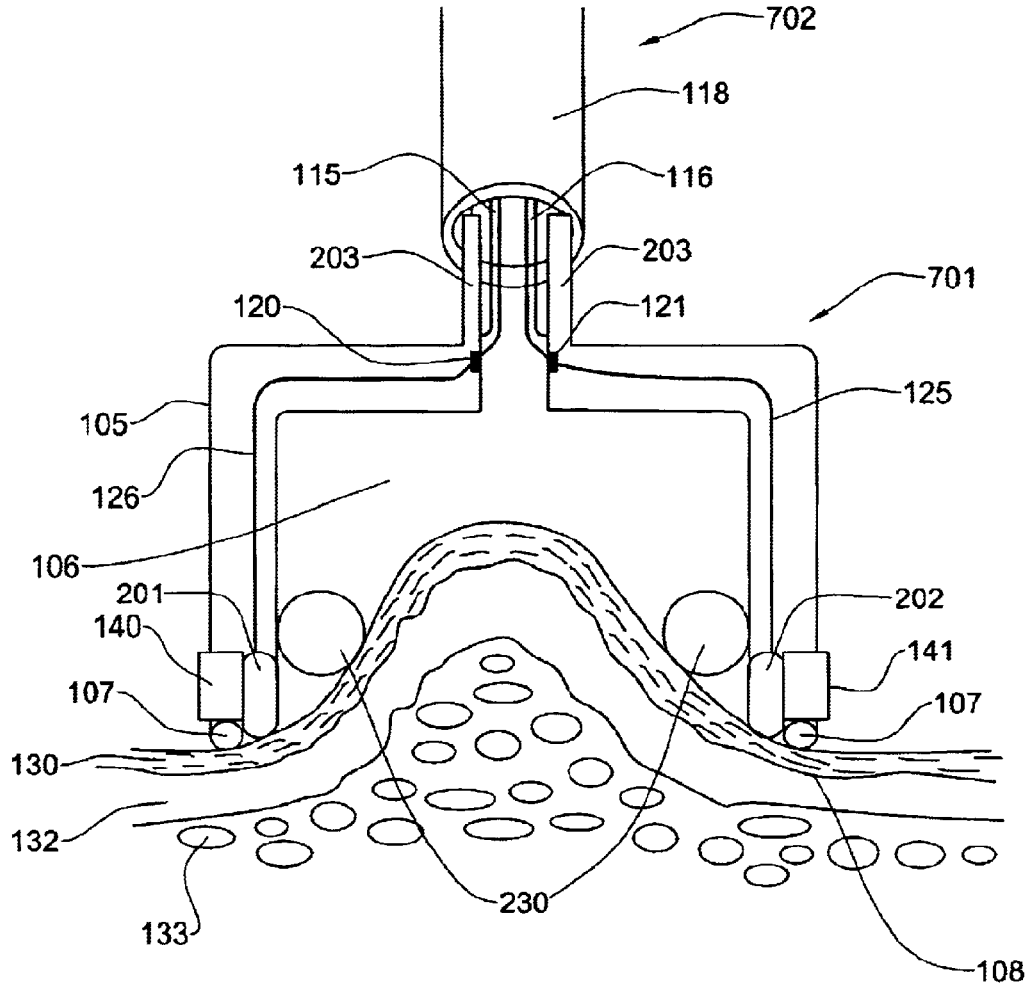

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-7 is confirmed.

Claim 8 is determined to be patentable as amended.

Claims 9-18, dependent on an amended claim, are determined to be patentable.

New claims 19-39 are added and determined to be patentable.

8. A system for treating skin, comprising:
(a) a skin deformer *for* deforming the skin so that a region of skin protrudes out from surrounding skin;
(b) one or more RF electrodes configured to apply RF energy to the [skins] *skin; and*
(c) a [massage] *massager* for massaging the skin.

19. *A system for treating skin, the system comprising: a housing defining a cavity having a first side and a second side; a first RF electrode on the first side of the cavity; a second RF electrode on the second side of the cavity, wherein the first RF electrode and the second RF electrode are arranged to apply RF energy to the skin; and a vacuum aperture in the housing for enabling a vacuum source to communicate with the cavity, wherein the cavity and the vacuum aperture cooperate to define a skin deformer, and wherein the vacuum aperture, the cavity, the first RF electrode, and second RF electrode are configured so that when an open end of the cavity is placed against the skin, the vacuum source is enabled to apply a negative pressure so that a skin deformation, caused by the negative pressure, protrudes out from surrounding skin between the first RF electrode and the second RF electrode,*
*wherein the system includes a massager having a curved surface associated with the housing and configured to massage the skin.*

20. *The system of claim 19, wherein the first RF electrode and the second RF electrode are arranged to apply RF energy to opposite sides of the protruding skin deformation.*

21. *The system of claim 20, wherein the RF energy ranges in frequency from 0.3 to 10 MHz.*

22. *The system of claim 20, wherein the RF energy ranges in power from 1 to 300 W.*

23. *The system of claim 19, wherein the protruding skin deformation includes a peak and opposing sides extending from the peak, and wherein the first RF electrode and the second RF electrode are arranged so that when the vacuum source is enabled to apply the negative pressure, the first RF electrode and the second RF electrode each lie adjacent a differing opposing side of the protruding skin deformation.*

24. *The system of claim 19, wherein the first RF electrode, the second RF electrode, and the cavity are configured such that when the vacuum source applies the negative pressure against the skin, subcutaneous adipose tissue is drawn toward the first RF electrode and the second RF electrode.*

25. *The system of claim 19, wherein the negative pressure ranges from 0.2 to 1 atmosphere.*

26. *The system of claim 19, wherein the first RF electrode and the second RF electrode are configured to be electrically connectable to a processor for measuring impedance across one or more of the first RF electrode and the second RF electrode.*

27. *The system of claim 26, wherein the processor is further configured to determine heat distribution in skin based upon one or more impedance measurements.*

28. *The system of claim 19, wherein the first RF electrode is located on a first edge of the first side of the cavity, the second RF electrode is located on a second edge of the second side of the cavity, and wherein the vacuum aperture, the cavity, the first RF electrode, and second RF electrode are configured so that when an open end of the cavity is placed against the skin, the vacuum source is enabled to apply the negative pressure to deform the skin.*

29. *The system of claim 19, wherein the housing is configured to communicate with a cooler for cooling skin.*

30. *The system of claim 19, wherein the massager having a curved surface associated with the housing includes curved surfaces on opposing sides of the housing.*

31. *A system for treating skin, the system comprising: a conduit configured for connection to a housing defining a cavity having a first side and a second side, the conduit and the cavity defining a skin deformer, wherein the housing supports a first RF electrode on the first side of the cavity and a second RF electrode on the second side of the cavity, wherein the first RF electrode and the second RF electrode are configured to apply RF energy to skin, and wherein a massager having a curved surface associated with the housing is configured to massage the skin;*
*a vacuum source configured to be connected to the conduit for drawing a vacuum in the cavity; and*
*a processor configured for enabling at least one of control and monitoring of at least one of negative pressure intensity and RF energy, so that when an open end of the cavity is placed against the skin, the vacuum source is enabled to apply a negative pressure so that a skin deformation, caused by the negative pressure, protrudes out from surrounding skin between the first RF electrode and the second RF electrode.*

32. *The system of claim 31, wherein the curved surface is associated with at least one of the first RF electrode and the second RF electrode.*

33. *The system of claim 31, wherein the processor is further configured to measure impedance across one or more of the first RF electrode and the second RF electrode.*

34. *The system of claim 31, further comprising an input interface for enabling entry of skin treatment parameters.*

35. *The system of claim 34, wherein the skin treatment parameters include at least one of RF energy pulse duration, RF energy frequency, RF energy power, and a delay time between cooling skin and application of RF energy.*

36. *The system of claim 31, wherein the processor is further configured to monitor the RF enemy passing through the first RF electrode and the second RF electrode.*

37. *The system of claim 31, wherein the first RF electrode is located on a first edge of the first side of the cavity, the second RF electrode is located on a second edge of the second side of the cavity, and wherein the conduit, the cavity, the first RF electrode, second RF electrode, and the processor are configured so that when an open end of the cavity is placed against the skin, the vacuum source is enabled to apply the negative pressure to deform the skin*

38. The system of claim 31, further comprising a cooler for cooling skin.

39. The system of claim 31, wherein the massager having a curved surface associated with the housing includes curved surfaces on opposing sides of the housing.

\* \* \* \* \*